United States Patent [19]
Dyckman et al.

[11] Patent Number: 6,025,530
[45] Date of Patent: Feb. 15, 2000

[54] PHENOL TAR CRACKING PROCESS

[75] Inventors: Arkady Samuilovich Dyckman; Andrey Zinenkov; Boris Issakovich Gorovits, all of St. Petersburg, Russian Federation; John W. Fulmer, Mt. Vernon, Ind.

[73] Assignee: General Electric Company, Schenectady, N.Y.

[21] Appl. No.: 09/018,662

[22] Filed: Feb. 4, 1998

[30] Foreign Application Priority Data

Feb. 28, 1997 [RU] Russian Federation ............ 97/103102

[51] Int. Cl.⁷ .......................... C07C 37/68; C07C 45/00
[52] U.S. Cl. ...................... 568/754; 568/383; 568/749; 568/750; 585/437; 585/469; 203/91
[58] Field of Search ...................... 568/383, 749, 568/750, 754; 585/437, 469; 203/91

[56] References Cited

U.S. PATENT DOCUMENTS

| | | |
|---|---|---|
| 3,850,996 | 11/1974 | Nixon . |
| 4,339,605 | 7/1982 | Ligorati et al. . |
| 5,283,376 | 2/1994 | Dyckman et al. . |
| 5,457,244 | 10/1995 | Dyckman et al. . |
| 5,504,251 | 4/1996 | Dyckman et al. . |
| 5,672,774 | 9/1997 | Dyckman et al. . |

FOREIGN PATENT DOCUMENTS

| | | |
|---|---|---|
| 0 168 358 A1 | 1/1986 | European Pat. Off. . |
| 0 713 850 A1 | 5/1996 | European Pat. Off. . |
| 2056400 | 3/1996 | Russian Federation . |
| 2079479 | 5/1997 | Russian Federation . |
| 715316A | 9/1954 | United Kingdom . |

OTHER PUBLICATIONS

EP Search Report for European Equivalent Application No. EP 98 30 1240.

*Primary Examiner*—James O. Wilson

[57] ABSTRACT

The present invention relates generally to a method for treating phenol tar, and, more particularly to a method for separating valuable products from phenol tar by treating the tar with steam.

16 Claims, 1 Drawing Sheet

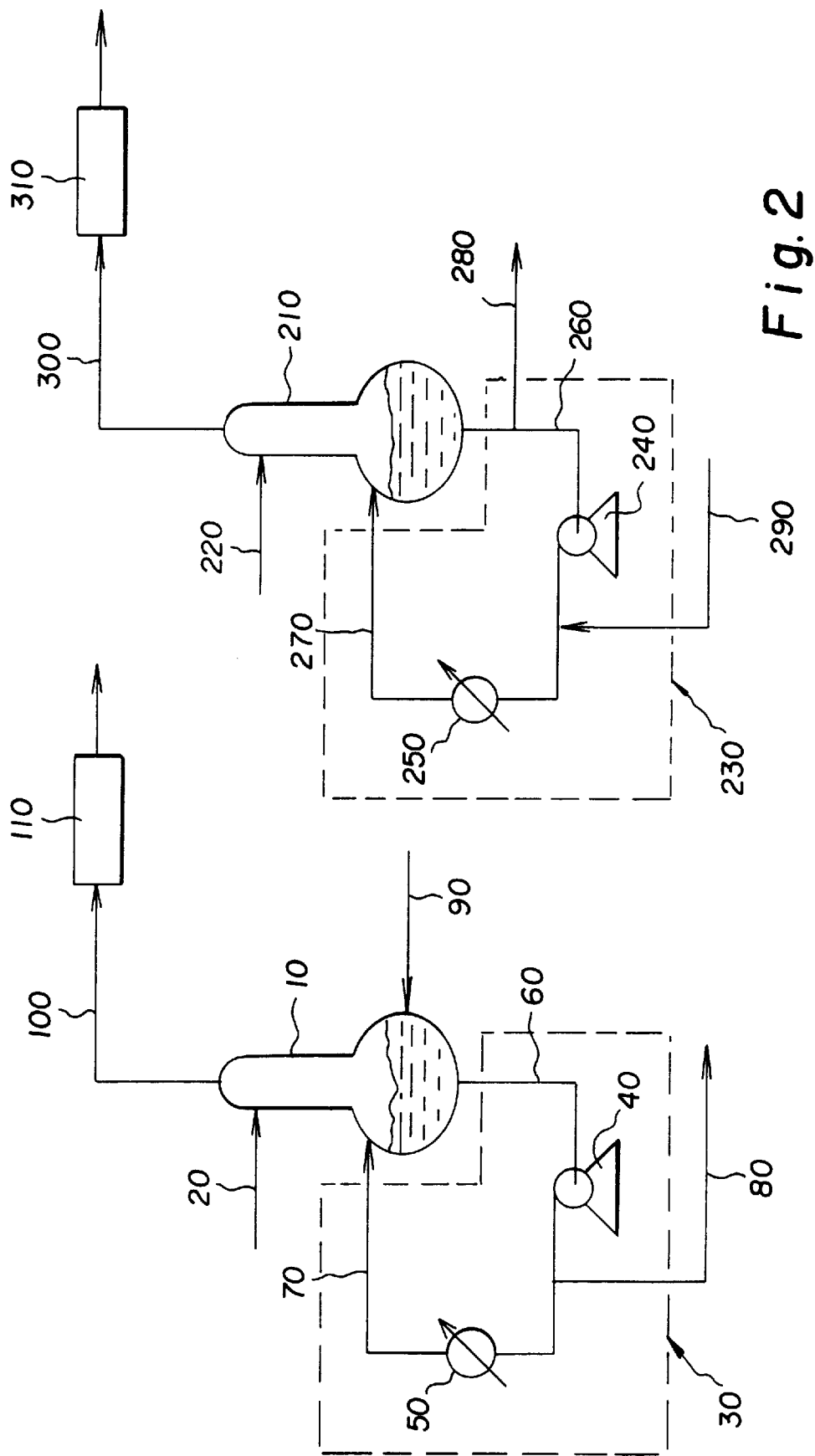

PHENOL TAR CRACKING PROCESS

This application claims priority rights under 35 U.S.C. 119 from Russian Application Serial No. 97/103,102 filed on Feb. 28, 1997.

BACKGROUND OF THE INVENTION

The present invention relates generally to a method for treating tar, and, more particularly to a method for separating valuable products from tar by treating the tar with steam. The present invention is particularly useful for separating valuable products from phenol tar and/or mixtures of phenol tar with bisphenol-A tar.

Phenol tar is a heavy, viscous byproduct produced in the industrial synthesis of phenol and acetone from cumene. Phenol tar is a complex mixture which comprises phenol, acetophenone, dimethylbenzyl alcohol, α-methyl styrene dimers, p-cumylphenol, small amounts of salts (principally $Na_2SO_4$) and many other chemicals in smaller amounts. It is difficult to dispose of phenol tar in an environmentally acceptable manner. Specifically, burning phenol tar is not a good disposal solution because it contains many ingredients which do not burn readily, such as phenol and $Na_2SO_4$. Therefore, a need exists to find more environmentally acceptable methods of disposing of phenol tar. The present invention reduces pollution resulting from the disposal of phenol tar by extracting valuable chemicals from the tar that can be recycled, thus reducing the amount of phenol tar that must be disposed of.

U.S. Pat. No. 3,850,996 (hereinafter "the '996 Patent"), describes a conventional method for disposing of phenol tar. Specifically, the '996 Patent describes a process wherein the phenol tar is thermally broken-down by heating it in a continuous operation column-type reactor (i.e., a thermocracker). The phenol tar is first fed into the middle part of the column type reactor. Upon heating, the phenol tar is refluxed, and the vapor which does not condense is led into a separation stage. The waste tar residue is removed from the bottom of the reactor. This process operates at a pressure of about 3.5 Bars, a reflux ratio of about 8, and a temperature of about 315° to 325° C. The composition of the phenol tar disclosed in the '996 Patent is described in Table 1 below.

TABLE 1

Phenol Tar Composition

| Component | Composition, weight % |
| --- | --- |
| Phenol | 15.4 |
| Acetophenone | 9.3 |
| Dimethylbenzyl alcohol | 9.1 |
| p-Cumylphenol | 40.9 |
| Heavy residue | 25.3 |

The vapor obtained from the process according to the '996 patent principally comprises the valuable products: cumene, phenol and α-methylstyrene. Acetophenone, another valuable product, remains almost entirely in the bottom of the reactor with the waste tar residue.

The process described in the '996 Patent has several disadvantages. Specifically, this process produces a relatively low total yield of valuable products (i.e., products which can be recycled), and a relatively high proportion of the phenol tar is converted to waste tar residue rather than to valuable products. Moreover, the success of this process is critically dependent upon the composition of the phenol tar fed into the process—the phenol tar must be concentrated in phenol, α-methylstyrene dimers, dimethylbenzyl alcohol and cumylphenol, which can decompose into valuable products such as phenol, α-methylstyrene, and cumene. The phenol tar described above in Table 1 is amenable to the process described in the '996 patent, and could theoretically yield 541 kg of valuable products per ton of phenol tar. However, a less rich phenol tar described below in Table 2, which is recited in Russian Patent No. 2,056,400, could theoretically only yield about 270 kg of valuable products per ton of phenol tar.

TABLE 2

Phenol Tar Composition

| Component | Composition, weight % |
| --- | --- |
| Light end components | <0.01 |
| Cumene | 0.01 |
| AMS | 0.1 |
| Phenol | 15.2 |
| Acetophenone | 22.8 |
| AMS | 8.2 |
| CP | 13.8 |
| Heavies | remainder to 100 |

Russian Patent No. 2,056,400, discloses a process for increasing the yield of valuable products from treating phenol tar by removing 50 to 100% of the acetophenone from the waste tar residue produced in a process analogous to that described in the '996 Patent. This is accomplished by adding bisphenol tar in a concentration of from 10 to 90% to the feedstock to provide the required pH (below about 7), and by reducing the reflux ratio to between 0.5 and 2.0. This technique can increase the total yield of valuable products by an additional 100 to 150 kg per ton of phenol tar, and has successfully produced up to 425 kg of valuable products per ton of phenol tar. However, it is noted that the success of this technique is highly dependent upon the composition of the phenol tar. Specifically, the phenol tar must be rich in phenol, α-methylstyrene dimers, dimethylbenzyl alcohol and cumylphenol, which can decompose into valuable products such as phenol, α-methylstyrene, and cumene. Generally, this method is disadvantageous because it results in a relatively low yield of valuable products.

Russian Patent Application No. 95-109134 suggests treating phenol tar with phosphoric acid that is pre-heated to between 50° C. and 180° C. This method is capable of producing up to 550 kg of valuable products per ton of phenol tar. However, this method produces a waste tar residue in the bottom of the reactor which comprises phosphoric acid and/or polyphosphoric acids. The presence of these acids in the waste tar leads to greater ash content in the smoke of the burned waste tar, and thus produces further pollution which makes this method undesirable in most situations.

SUMMARY OF THE INVENTION

There is provided, in accordance with the invention, an improved process for disposing of tar which does not possess the shortcomings of the prior art, and offers the advantage of efficiently extracting valuable chemicals from the tar that can be recycled, thus reducing the amount of phenol tar that must be disposed of. Specifically, there is provided a process for disposing of tar wherein the tar is treated with water. This process reduces pollution resulting from the disposal of tar.

In a preferred embodiment of the process according to the invention, the tar is converted into valuable products and waste tar by a process which comprises:

(a) introducing tar into a reactor;

(b) heating the tar, thereby forming valuable products and waste tar;

(c) simultaneously treating the tar with steam for a sufficient residence time to increase the proportion of the tar converted into valuable products and decrease the proportion of the tar converted into waste tar; and (d) separating the valuable products from the waste tar.

In a particularly preferred embodiment, the tar is either (1) phenol tar, or (2) a mixture of both phenol tar and bisphenol-A tar.

These and other features, aspects and advantages of the present invention will become better understood with reference to the following description, the appended claims, and the accompanying drawings.

BRIEF DESCRIPTION OF THE DRAWINGS

FIG. 1 is a schematic view of an embodiment of an apparatus that may be used to carry out the process of the invention.

FIG. 2 is a schematic view of a second embodiment of an apparatus that may be used to carry out the process of the invention.

DESCRIPTION OF THE PREFERRED EMBODIMENTS

In FIG. 1, a vertically oriented thermal cracker unit 10 is connected to a phenol tar input tube 20. The thermal cracker 10 is also connected to a heated recirculating loop 30 which comprises a pump 40 and a heater 50. The input pipe 60 of the recirculating loop 30 is connected to the thermocracker unit 10 at a position below that of the output pipe 70. The recirculating loop 30 is also connected to a waste tar exit pipe 80. A water/steam input pipe 90 is connected to the thermal cracker 10 at a position sufficiently low such that when the process is operating, the water/steam will be injected into the phenol tar. A vapor exit pipe 100 is also positioned at the topmost end of the vertically oriented thermal cracker unit 10, and joins the thermal cracker unit to valuable product condensing means 110.

In FIG. 2, a second apparatus is shown that is identical to the apparatus shown in FIG. 1, with the exception that the water/steam input pipe 290 is connected to the recirculating loop 230.

In operation, referring again to the embodiment of the invention shown in FIG. 1, tar is injected through the tar input tube 20 into the thermocracker unit 10. The tar settles in the bottom of the thermocracker unit 10 and water/steam is injected into the tar through the water/steam input pipe 90. The injected water/steam may be preheated. During this process, the tar/water mixture is withdrawn from the thermocracker unit 10, through the input pipe 60, into the recirculation loop 30. In the recirculation loop 30, the tar/water mixture passes through a pump 40 and a heater 50, before being injected through the output pipe 70 back into the thermocracker unit 10. The heated tar/water mixture is thus refluxed within the thermocracker unit 10, and a portion of the vapor is withdrawn from the top of the thermocracker unit 10 via the vapor exit pipe 100. This vapor is condensed in the valuable product condenser 110 to obtain the desired valuable products, which may be recycled. The waste tar may be withdrawn from the recirculation loop through the waste tar exit pipe 80.

The operation of the embodiment shown in FIG. 2 is identical to that of the embodiment shown in FIG. 1, with the exception that the water/steam is injected into the recirculation loop 230 instead of directly into the thermocracker unit 210. All reference numbers correspond to those in the embodiment shown in FIG. 1, adding 200 to each number.

The process described above is preferably conducted by maintaining a temperature of 300 to 340° C., and a pressure of less than 3 Bars within the thermocracker unit. External heat and/or pressure can be applied to achieve these conditions.

The thermocracker unit is preferably a column-type reactor. The valuable products obtained via the valuable product condensing means typically comprise phenol, α-methylstyrene, and cumene when phenol tar is treated. It is preferable to introduce between 1 and 15% by weight of water relative to the weight to the phenol tar. The above-described process may optionally be conducted in the presence of bisphenol tar (i.e., the heavy waste product formed in Bisphenol-A production according to the known method of producing Bisphenol-A from phenol and acetone).

Without wishing to be limited to any one theory of operation of the invention, it is thought that the embodiments described above improve the yield of valuable products by increasing the vapor/liquid ratio in the reactor, which increases the surface area, and consequently increases the evaporation rate of the valuable products, which are mostly lower boiling substances than those found in the viscous waste tar. This increased evaporation rate is thought to cause bubbles comprising valuable product vapors to rise more rapidly through the hot, viscous tar liquid. These rapidly rising bubbles are exposed to the tar for a shorter period of time, which reduces the probability that the valuable products in the bubbles will recombine with the tar before escaping. For example, vaporized α-methylstyrene may dimerize or recombine with phenol in the tar if it does not escape rapidly from the tar. Thus, it is thought to be important for the water/steam to have sufficient residence time in the tar to increase the evaporation rate of the valuable products. For these reasons, adding water/steam results in a lower concentration of low-boiling light products, which are mostly valuable products, in the liquid in the bottom of the reactor, and reduces secondary condensation processes. Another advantage of this method is thought to be that the increase of linear stream velocity in the reboiler due to the addition of water reduces the probability of fouling the reboiler with viscous, heavy waste tar.

The addition of water according to this method increases the total yield of valuable products by 10 to 50 kg per ton of phenol tar processed, and reduces the amount of waste tar which must be combusted by the same value. The water may be obtained from existing processes required in a phenol production plant.

The treatment of tar according to some preferred embodiments of the invention is illustrated by the following examples.

EXAMPLE 1

Phenol tar was processed using a bench-top unit similar to the embodiment described in FIG. 1, with the exception that a recirculating loop was not present. This embodiment consisted of a 1 liter pot equipped with an electric heater, a column reactor, a level sensor, a thermocouple, a water injector, and a heated valve for withdrawing the bottom liquid. The column which had a thermo-insulating coating, was attached to the pot. A side fitting was attached to the column, and was used to introduce phenol tar into the reactor. A condenser was used above the reactor to ensure that some of the vapor would return to the pot during refluxing. The composition of the Phenol tar introduced is described in table 2, above.

During the experiment, the phenol tar was fed into the reactor at a continuous rate of 100 ml per hour. The distillate was continuously removed, and the waste tar was removed at equal intervals, with each removal not exceeding 5% of the total liquid present in the bottom pot. The temperature of the pot was maintained at 315° C., the pressure at 2.75 Bar (absolute), and the reflux ratio at 2. One percent water by weight of phenol tar was introduced into the reactor. The results of the experiments are summarized in Table 4, where the product yields have been recalculated for 1000 Kg of tar.

EXAMPLE 2

The process was performed as described in Example 1 with the exception that the amount of water added was 8% by weight of the phenol tar introduced into the reactor. Also, the reactor temperature was maintained at 340° C., the pressure was 3 Bar (absolute), and the reflux ratio was 0.5.

EXAMPLE 3

The process was performed as described in Example 1 with the exception that the amount of water added was 15% by weight of the phenol tar introduced into the reactor. Also, the reactor temperature was maintained at 300° C., and the pressure was 3 Bar (absolute).

EXAMPLE 4

The process was performed as described in Example 1 with the exception that the amount of water added was 2.5% by weight of the phenol tar introduced into the reactor. Also, the reactor temperature was maintained at 315° C., and the pressure was 3 Bar (absolute). Thirty percent bisphenol-A tar was added to the phenol tar in this experiment. The type of bisphenol-A tar is disclosed in U.S. Pat. No. 5,672,774 at Table 3, which is incorporated by reference herein.

COMPARATIVE EXAMPLE 5

The process was performed as described in Example 1 with the exception that no water was introduced into the reactor.

EXAMPLE 6

Phenol tar having a composition as described in Table 3, was treated using an apparatus similar to that embodiment described in FIG. 2, with the exception that the steam/water was injected into the recirculation loop after the pump, and the waste tar was removed before the pump. This apparatus was constructed by modifying the apparatus described in Example 1.

During the experiment, the phenol was fed into the reactor at a continuous rate of 100 ml per hour. The distillate was continuously removed, and the waste tar was removed at equal intervals, with each removal not exceeding 5% of the total liquid present in the bottom pot. The temperature of the pot was maintained at 315° C., the pressure at 2.75 Bar (absolute) and the reflux ratio at 2. Eight percent water by weight of phenol tar was introduced into the reactor during the experiment.

TABLE 3

Phenol Tar Composition

| Component | Composition, weight % |
|---|---|
| Light end components | <0.01 |
| Cumene | 0.02 |
| α-methylstyrene | 0.1 |
| Phenol | 16.7 |
| Acetophenone | 15.6 |
| Dimethyl Benzyl Alcohol | 5.5 |
| Dimers of α-methylstyrene | 5.8 |
| P-Cumylphenol | 15.4 |
| Heavy end components | 40.9 |

Results

The results of Examples 1–6 are presented in Table 4 below:

TABLE 4

Phenol Tar Thermocracking

| | Example | | | | | |
|---|---|---|---|---|---|---|
| | 1 | 2 | 3 | 4 | 5 | 6 |
| Component | Amount in distillate per 1000 kg of feed | | | | | |
| Light end components | 18 | 25 | 19 | 18 | 17 | 33 |
| cumene | 53 | 83 | 69 | 56 | 46 | 128 |
| α-methylstyrene | 67 | 71 | 63 | 66 | 63 | 139 |
| Phenol | 229 | 244 | 224 | 240 | 228 | 167 |
| Acetophenone | 116 | 228 | 121 | 144 | 136 | 89 |
| TYVP* | 349 | 387 | 356 | 352** | 337 | 436 |
| Acetophenone in distillate, % of it in feed | 51 | 100 | 53 | 63 | 58 | 57 |

*Total Yield Valuable Products
**This value represents the calculated TYVP resulting from the phenol tar alone. The measured TYVP was 652, but this included contributions from both the phenol tar and the bisphenol-A tar included in Example 4.

The results shown in Table 4 prove that adding even 1% water improved the total yield of valuable products produced from the phenol tar treatment process (compare Examples 1 and 5). Example 2, where 8% water was added, showed a better result than Examples 1 and 3 where 1% and 15% water, respectively, were added. Example 4 shows that the invention may be employed with a mixture of phenol tar and bisphenol-A tar. Comparative Example 5, where no water was added, showed the poorest performance, thus proving the usefulness of the invention. Example 6, where the water/steam was injected into the recirculation loop, exhibited the best performance.

Many other variations and modifications of the invention will be apparent to those skilled in the art without departing from the spirit and scope of the claimed invention. For example, the apparatus for performing the claimed process depicted in FIG. 1 could incorporate a pipe to remove the waste tar directly from the reactor rather than from the recirculation loop. Also, the process could be used to treat other types of tar. Therefore, the spirit and scope of the appended claims should not be limited to the description of the preferred versions contained herein.

What is claimed is:

1. A tar processing method for converting and separating phenol tar into valuable products and waste tar consisting essentially of:

(a) introducing tar into a reactor;

(b) heating the tar, thereby forming valuable products and waste tar;

(c) simultaneously treating the tar with steam for a sufficient residence time to increase the proportion of the tar converted into valuable products and decrease the proportion of the tar converted into waste tar; and (d) separating the valuable products from the waste tar.

2. The tar processing method according to claim 1, wherein the tar comprises phenol tar.

3. The tar processing method according to claim 2, wherein the tar further comprises bisphenol-A tar.

4. The tar processing method according to claim 2, wherein the phenol tar is heated by passing it through a heated recirlculating loop connected to the reactor.

5. The tar processing method according to claim 4, wherein the steam is injected into the heated recirculating loop.

6. The tar processing method according to claim 4, wherein the steam is injected directly into the reactor.

7. The tar processing method according to claim 1, wherein the amount of steam added to the tar is 1% to 15% by weight of the phenol tar introduced into the reactor.

8. The tar processing method according to claim 7, wherein the absolute pressure within the reactor is less than 3 bar.

9. The tar processing method according to claim 8, wherein the temperature is from 300° C. to 340° C.

10. A process for treating tar comprising exposing the tar to steam at a pressure of less than 3 bars.

11. The process according to claim 10, wherein the tar comprises phenol tar.

12. The process according to claim 11, wherein the tar further comprises bisphenol-A tar.

13. The process according to claim 10, wherein the amount of steam added to the tar is 1% to 15% by weight of the phenol tar.

14. The process according to claim 13, wherein the absolute pressure of the phenol tar and steam is less than 3 bar.

15. The process according to claim 14, wherein the temperature of the phenol tar and steam is from 300° C. to 340° C.

16. A tar processing method for converting and separating phenol tar into valuable products and waste tar comprising:

(a) introducing tar into a reactor;

(b) heating the tar, thereby forming valuable products and waste tar;

(c) simultaneously treating the tar with steam at a pressure of less than 3 bars for a sufficient residence time to increase the proportion of the tar converted into valuable products and decrease the proportion of the tar converted into waste tar; and (d) separating the valuable products from the waste tar.

* * * * *